(12) United States Patent
Wiersma

(10) Patent No.: US 11,247,074 B2
(45) Date of Patent: Feb. 15, 2022

(54) SYSTEMS AND METHODS FOR DETERMINING 6DOF CORRECTION TRAJECTORIES IN COMPENSATING MOVEMENT OF A TREATMENT TARGET IN A PATIENT

(71) Applicant: Rodney Wiersma, Chicago, IL (US)

(72) Inventor: Rodney Wiersma, Chicago, IL (US)

( * ) Notice: Subject to any disclaimer, the term of this patent is extended or adjusted under 35 U.S.C. 154(b) by 374 days.

(21) Appl. No.: 15/963,962

(22) Filed: Apr. 26, 2018

(65) Prior Publication Data

US 2019/0329074 A1 Oct. 31, 2019

(51) Int. Cl.
*A61N 5/10* (2006.01)
*A61B 34/30* (2016.01)
*A61G 13/04* (2006.01)

(52) U.S. Cl.
CPC .......... *A61N 5/1083* (2013.01); *A61B 34/30* (2016.02); *A61G 13/04* (2013.01); *A61N 5/107* (2013.01); *A61B 2034/304* (2016.02)

(58) Field of Classification Search
CPC .... A61N 5/1083; A61N 5/107; A61N 5/1049; A61B 34/30; A61B 2034/304; A61G 13/04
See application file for complete search history.

(56) References Cited

U.S. PATENT DOCUMENTS 8,042,209 B2    10/2011    D'Souza et al.
2010/0041938 A1 *  2/2010    Stoianovici ........ A61B 17/3468
                                                             600/7
2011/0291028 A1 *  12/2011    Brand ................. A61N 5/103
                                                             250/492.1

(Continued)

OTHER PUBLICATIONS

J. Somló and J. Molnár, "Time-optimal motion planning for robots," 19th International Workshop on Robotics in Alpe-Adria-Danube Region (RAAD 2010), Budapest, 2010, pp. 11-23, doi: 10.1109/RAAD.2010.5524615. (Year: 2010).*

(Continued)

*Primary Examiner* — Jeff A Burke
*Assistant Examiner* — Joshua Alexander Garza
(74) *Attorney, Agent, or Firm* — Gearhart Law LLC; David Postolski, Esq.

(57) ABSTRACT

Disclosed herein are system, method, and computer program product embodiments a 6 degree-of-freedom (6DoF) correction trajectory in order to compensate movement of a treatment target in a patient supported by a patient support end-effector. An embodiment operates by receiving a starting end-effector position, a starting clinical target position, and a target destination position. The target destination position corresponds to a position in space receiving targeted treatment from a treatment delivery device. The embodiment determines a destination end-effector position in 6DoF associated with the end-effector that would cause the target to be positioned on the target destination position. A trajectory is calculated between the starting end-effector position and the destination end-effector position. The embodiment transmits, to a mechanical device controlling movement of the end-effector, one or more signals causing the end-effector to move from the starting end-effector position to the destination end-effector position along the determined trajectory.

13 Claims, 10 Drawing Sheets

(56) References Cited

U.S. PATENT DOCUMENTS

2017/0232274 A1* 8/2017 Isola ................ A61N 5/1037
                                                    600/1
2018/0015306 A1* 1/2018 Maurer, Jr. ......... A61B 6/4014
2019/0015685 A1* 1/2019 Ostyn ................ A61F 5/37

OTHER PUBLICATIONS

Zhu et al., L-BFGS-B—FORTRAN Subroutines for Large-Scale Bound Constrained Optimization, Dec. 31, 1994.
Park et al., ITOMP: Incremental Trajectory Optimization for Real-time Replanning in Dynamic Environments, Association for the Advancement of Artificial Intelligence (2012).
Lampariello et al., Trajectory planning for optimal robot catching in real-time, 2011 IEEE International Conference on Robotics and Automation (ICRA).

* cited by examiner

SYSTEMS AND METHODS FOR DETERMINING 6DOF CORRECTION TRAJECTORIES IN COMPENSATING MOVEMENT OF A TREATMENT TARGET IN A PATIENT

BACKGROUND

Technical Field

Embodiments generally relate to the treatment of tissues in a living organism, and in particular to moving a treatment delivery device end effector, to compensate for tissue movement relative to the treatment delivery device caused by biological activity of the organism, such as head or respiration motion, during treatment delivery, such as during delivery of a dose of radiation.

Background

Many medical procedures require the application of a treatment to a patient in localized areas and limited doses with a high degree of precision. As an example, radiation-based treatments have been used for many years to treat and diagnose patients. Planar X-ray radiographs, computed tomography (CT), and, stereostatic radiosurgery (SRS) are all examples of radiation-emitting procedures. SRS is a therapy modality used for the treatment of brain disorders by the use of highly precise radiation dose placement. The intent is to destroy the tumor or control its growth without harming nearby healthy brain tissue. Unlike conventional open brain surgery, SRS allows access to sites that would otherwise be difficult or inadvisable to treat due to potential surgical complications to nearby nerves, arteries, and other vital structures. SRS holds several advantages over surgical resection in that patients can go home the same day and experience significantly faster recovery times.

However, current SRS methods suffer from many challenges. SRS requires higher radiation dose and patient positioning tolerances than conventional radiation therapy. One method involves the use of a metal head ring that is rigidly fixated to the patient's skull using four pins under local anesthesia, and then bolted on a treatment couch. This immobilization locks the head into a precise stereotactic position, suppressing both voluntary and involuntary physiological motion. Placing and removing this frame is an invasive process that requires special expertise from additional support staff such as a neurosurgeon. The discomfort, inconvenience, anxiety and invasive nature associated with the frame have been identified as a serious cause of poor patient compliance and poor clinical efficiencies when SRS is medically indicated.

An alternative method involves the use a frameless solution where immobilization is implemented through the use of a customized extruded polystyrene foam (e.g., Styrofoam®) head mold together thermoplastic face masks. However, even with the mask, the patient's head can still significantly drift from left to right due to rotation about the fulcrum at the back of the skull. Additionally, it has been reported that many patients find the thermoplastic mask invasive and psychologically confining as it greatly restricts natural head motion.

SUMMARY

Disclosed herein are system, method, and computer program product embodiments for performing a 6 degree-of-freedom (6DoF) correction trajectory in order to compensate movement of a treatment target by moving a treatment delivery device end-effector. An embodiment operates by receiving a starting end-effector position, a starting clinical target position, and a target destination position. The target destination position corresponds to a position in space receiving treatment from a treatment delivery device. The embodiment determines a destination end-effector position in 6DoF associated with the end-effector that would cause the target to be positioned on the target destination position. A trajectory between the starting end-effector position associated with the end-effector and the destination end-effector position associated with the end-effector is calculated based on a 6DoF trajectory in the target space that interpolates between a starting clinical target position and a target destination position, or is calculated by solving a problem under both the mechanical actuator constraints and system dynamical constraints. An objective may be to find a target trajectory between the starting clinical target to the target destination position that is optimal both spatially and temporally such that the target is returned to the destination position as quickly as possible while following a path that is as short as possible, or the time integral of target position error along the trajectory in the target space is as small as possible. The embodiment transmits, to a mechanical device controlling movement of the end-effector, one or more signals causing the end-effector to move from the starting end-effector position to the destination end-effector position along the determined trajectory.

The embodiments disclosed above are only examples, and the scope of this disclosure is not limited to them. Particular embodiments may include all, some, or none of the components, elements, features, functions, operations, or steps of the embodiments disclosed above. Embodiments according to the invention are in particular disclosed in the attached claims directed to a method, a storage medium, a system and a computer program product, wherein any feature mentioned in one claim category, e.g. method, can be claimed in another claim category, e.g. system, as well. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

BRIEF DESCRIPTION OF THE DRAWINGS

The accompanying drawings are incorporated herein and form a part of the specification.

DETAILED DESCRIPTION

Provided herein are system, method and/or computer program product embodiments, and/or combinations and sub-combinations thereof, for performing a 6 degree-of-freedom (6DoF) correction trajectory in order to compensate movement of a treatment target in a patient supported by a patient support end-effector. As an example, embodiments may be used to perform real-time motion stabilization for stereostatic radiosurgery and other radiation-emitting medical procedures. While the embodiments described herein are exemplified in the context of particular procedures (e.g., cranial radiosurgery), they are generally applicable to any system that requires motion stabilization for clinical treatment.

Figure 1:
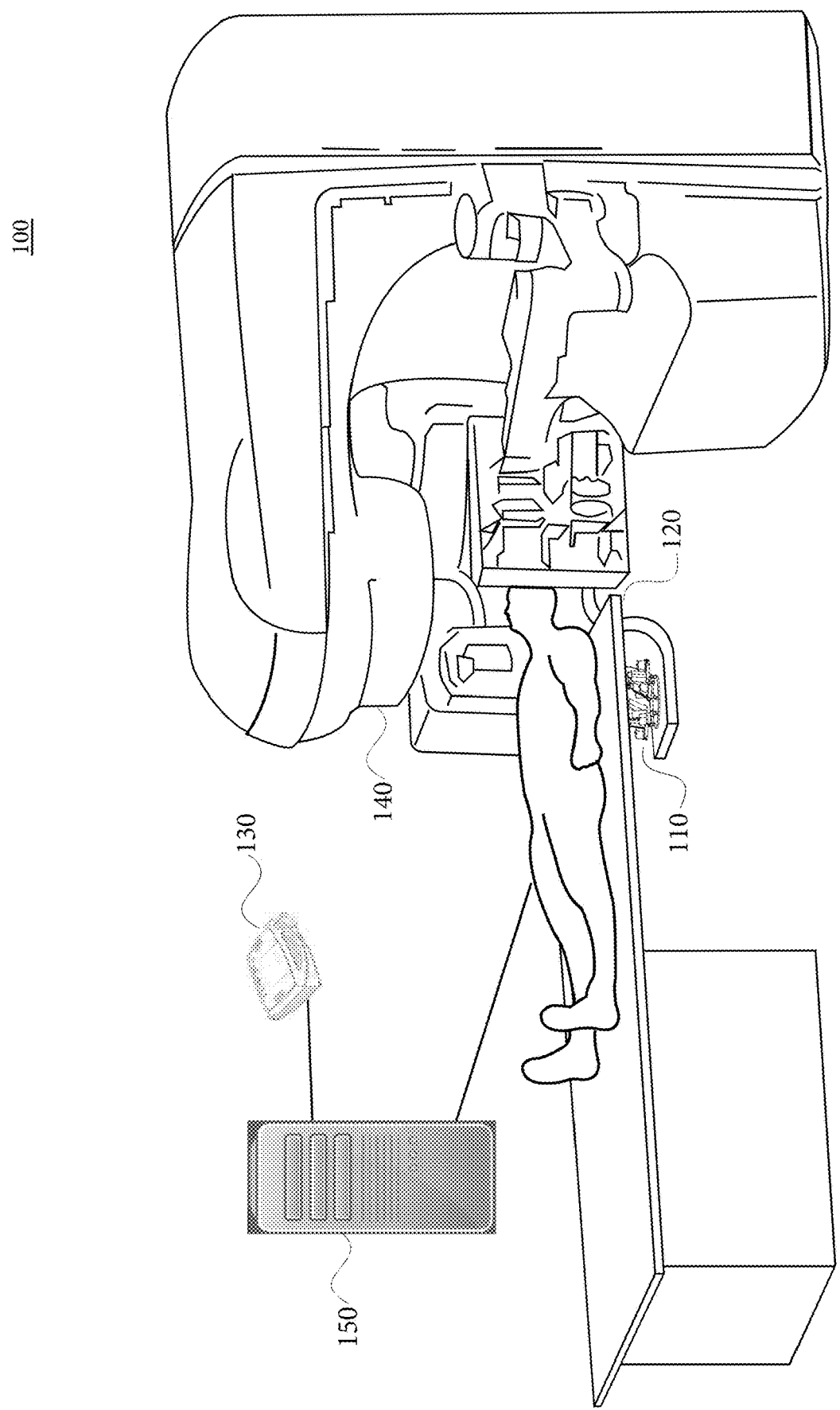
FIG. 1 illustrates a system for performing treatment procedures, according to an example embodiment.

FIG. 1 illustrates a system 100 for performing a medical procedure, according to an example embodiment. In particular embodiments, system 100 may include a kinematics robot 110, a patient support or end-effector surface 120, a movement tracking sensor 130, a treatment delivery device 140, and a computing device 150. Kinematics robot 110 may be operatively coupled to support surface 120 to adjust the positioning of support surface 120. In particular embodiments, kinematics robot 110 may adjust the position of support surface 120 along translational (x, y, z) and rotational (pitch, roll, yaw) axes, i.e., six degrees of freedom (6DoF). Support surface 120 may be any suitable mobile surface or mobile support system for supporting and adjusting the movement and positioning of a clinical target 122 for treatment procedures. As an example, support surface 120 may be configured to support a body part of a patient receiving radiosurgery or other suitable treatment, e.g., the head of a patient receiving intracranial radiosurgery to treat a brain tumor. By way of example, support surface 120 may be contoured to the shape of a person's head, may be a flat surface to support a patient's torso, etc. In particular embodiments, end-effector surface 120 and clinical target 122 are weakly coupled, that is, the clinical target rests on the surface and stays in contact with the surface by virtue of the target's weight, without external fixating means, such as frames, wires, etc. As such, the target may move more frequently and in less predictable ways than a target that is fixated to the end-effector surface.

Figure 2A:
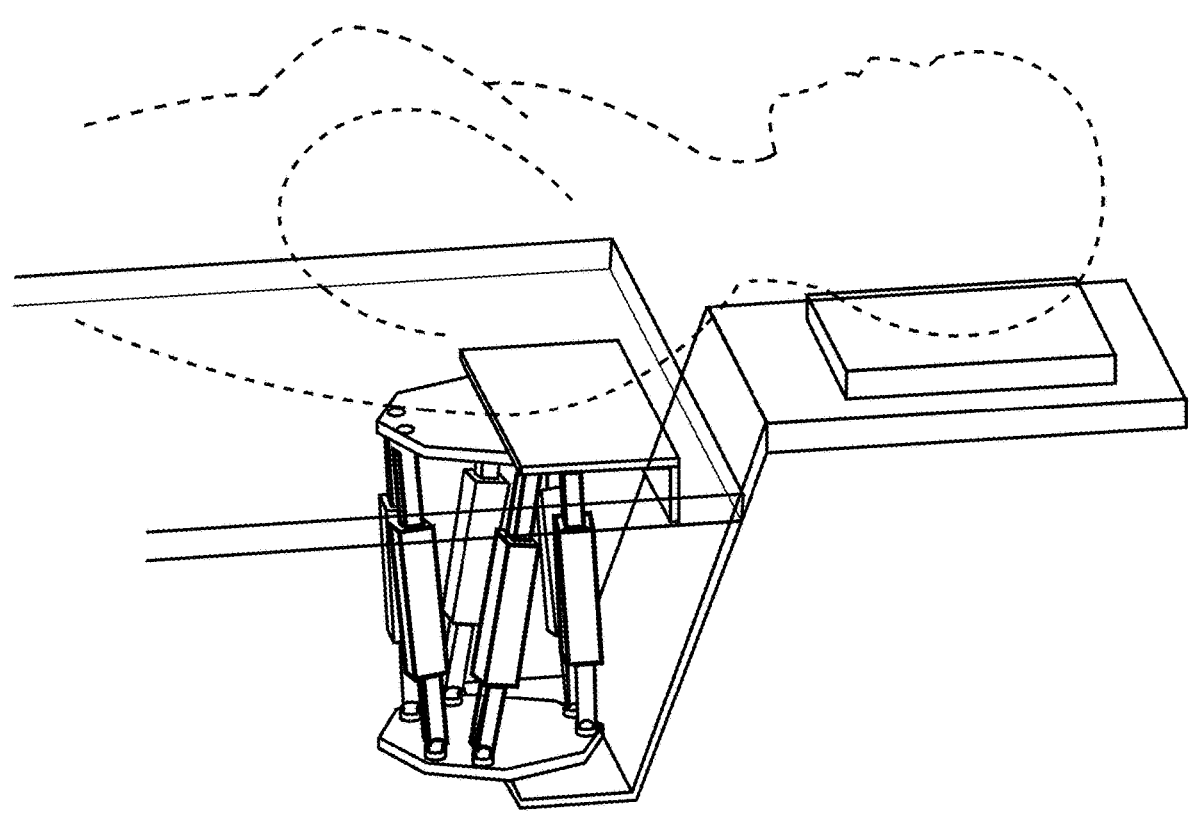
FIG. 2A illustrates system set-up including a kinematics robot configured to move a patient's head, according to an example embodiment.
Figure 2B:
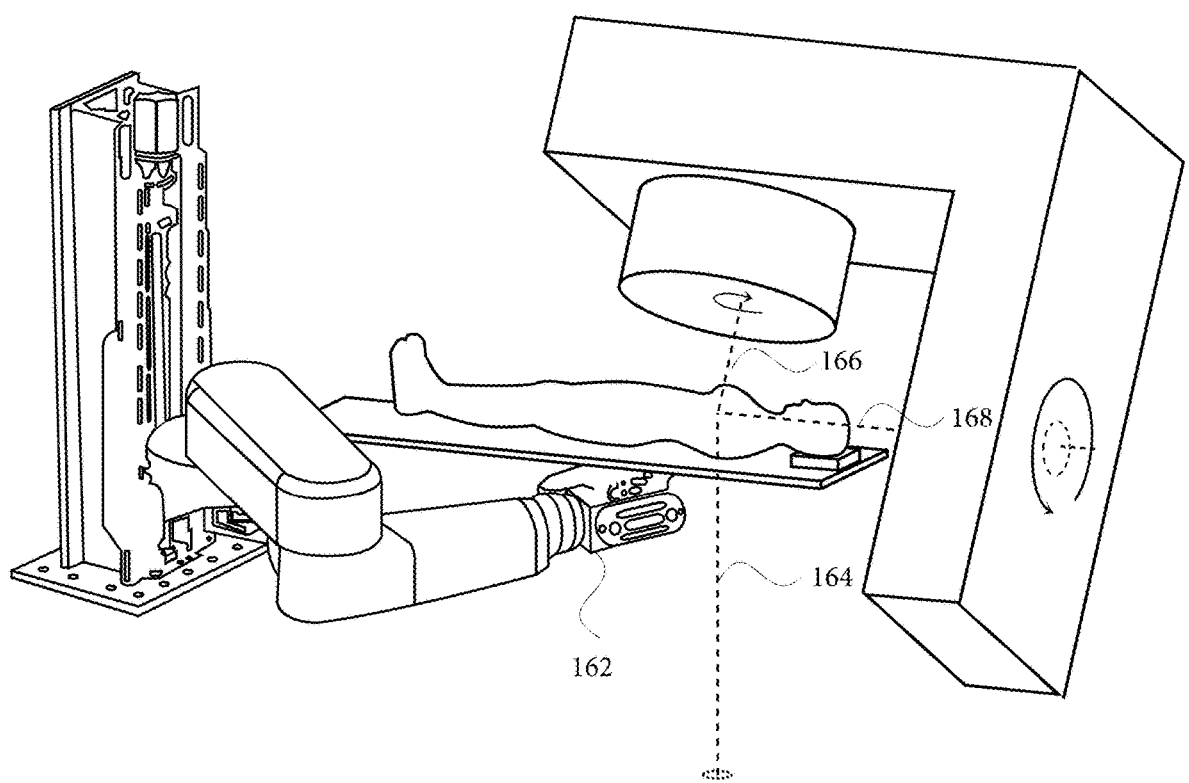
FIG. 2B illustrates system set-up including a kinematics robot configured to move a patient's entire body, according to an example embodiment.

FIGS. 2A and 2B show different example setups including kinematics configured to move a patient receiving a treatment. The set-up in FIG. 2A may be used, as an example, to provide treatment to a patient's head (e.g., radiation from a radiation beam). During the procedure, the patient may move out of position for various reasons, such as breathing or drifting out of position over time. In this example, a kinematics robot 110 may be used to move the patient's head to a desired position in 6DoF, as explained below with reference to FIG. 3.

The set-up shown in FIG. 2B may be used to move a patient's entire body while receiving treatment. In this example, a patient may be receiving lung radiation treatment for lung tumors. Again, a patient receiving treatment may move out of position. A treatment set-up 160 may include a combination of kinematic elements that allow for real-time or quasi-real-time movement of the patient in 6DoF. As an example, a robot 162 may be configured with rails that allow for movement on X and Y axes parallel to the floor, and a lift that moves the platform up and down along a Z axis. Additional kinematics may rotate the platform about a yaw axis 164, a pitch axis 166, and a roll axis 168, thus providing 6DoF movement. Although the particular patient movement setups referenced in FIGS. 2A and 2B have been described, this disclosure contemplates any suitable setup of system 100 configured to move a patient or a patient's body part in 6DoF as described throughout this disclosure. While reference is being made to "real-time" movement or "real-time" movement compensation throughout this disclosure, it should be understood that "real-time" movement can commonly carry some amount of delay and may be made of a series of consecutive movements over discrete time periods. As such, "real-time" and "quasi-real-time" are used interchangeably and meant to encompass any variations that can be fairly described as "real-time" by those skilled in the art.

Figure 3:
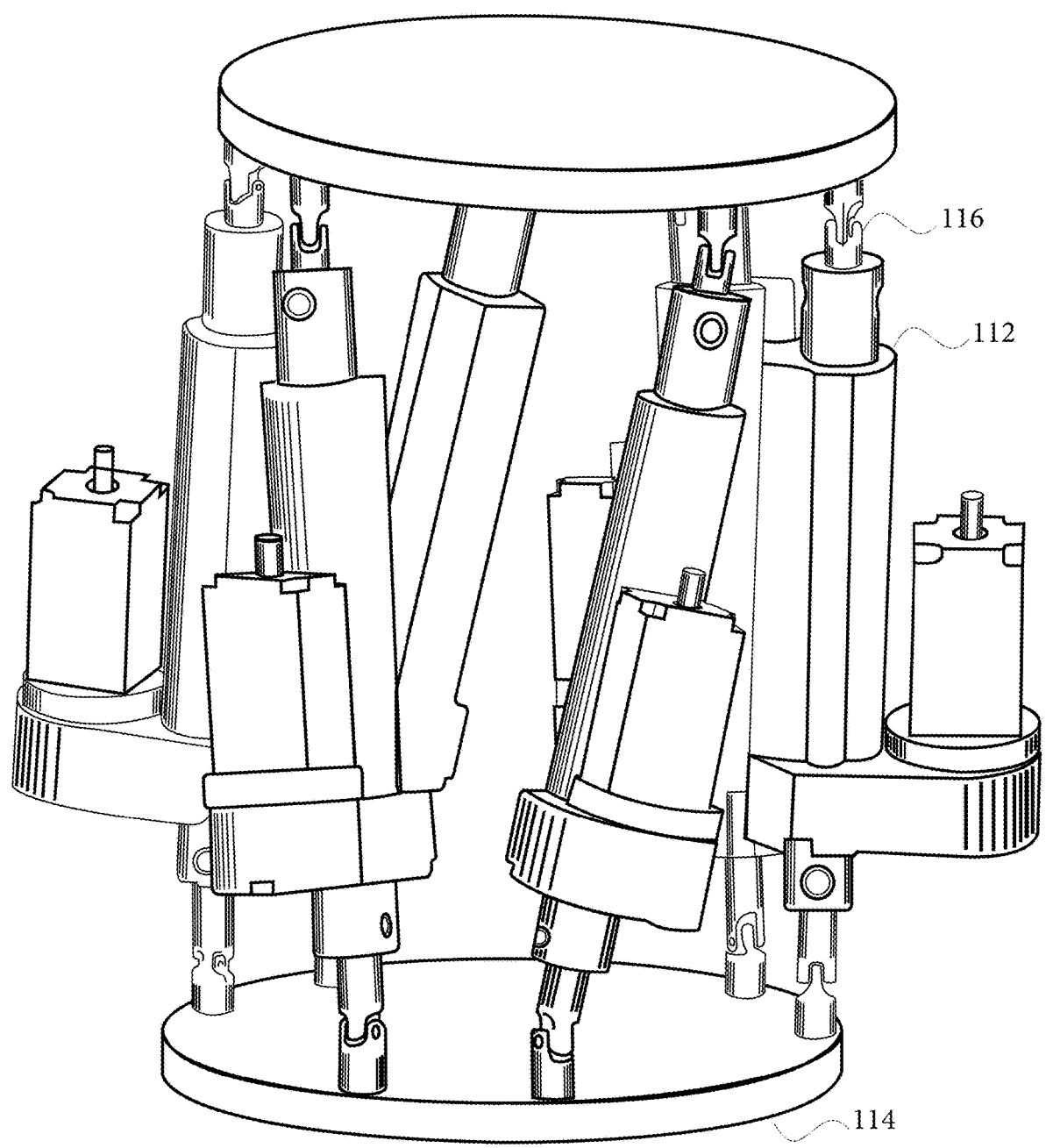
FIG. 3 illustrates a kinematics robot for moving an end-effector surface, according to an example embodiment.

FIG. 3 illustrates a kinematics robot 110 for moving end-effector surface 120, according to an example embodiment. Kinematics robot 110 may be any suitable mechanical device for controlling the movement of end-effector surface 120 to perform the methods described herein. In particular embodiments, kinematics robot 110 may employ parallel kinematics to perform 6DoF motions of a mobile top platform (e.g., end-effector platform 120) relative to a stationary bottom platform 114 using inverse kinematics control. In particular embodiments, kinematics robot 110 may include six linear actuators 112 connecting the bottom fixed plate 114 to an upper mobile platform. Universal joints 116 may connect the actuators to the top and bottom platforms, allowing free rotational movement at the joint position for full 6DoF capabilities of the end-effector platform 120. Kinematics robot 110 may cause movement of end-effector platform 120 based upon the linear trajectories of each of the six linear actuators 112.

Computing device 150 may obtain input from kinematics robot 110 and movement sensor 130, and may transmit instructions to operate the linear actuators 116 of kinematics robot 110 responsive to movements of the target 122. Movement sensor 130 may be any suitable device for measuring movement of clinical target 122 in real-time or near real-time. By way of example, movement sensor 130 may be a camera, an infrared camera, an accelerometer, a gyroscope, or any combination thereof. In particular embodiments, infrared markers may be attached to a patient to enhance an infrared camera's motion sensing and measuring accuracy. Computing device 150 may be any computing device comprising one or more processors and memory suitable for obtaining input from sensors, performing motion compensation computations, and output control signals, as described throughout this disclosure. By way of example, computing device 150 may be a general-purpose computer, special-purpose computer, personal computer, mobile computer, laptop computer, mobile phone, smartphone, personal digital assistant, tablet computer, etc, or any combination thereof.

While this disclosure primarily describes movement of a platform 120 with respect to a stationary treatment delivery device 140, it should be understood the same principles can be applied to embodiments where the treatment delivery device 140 is an end-effector moved by a kinematics robot 110 and a patient platform is kept stationary. The same methods and systems described above and below can be used to perform 6DoF correction trajectory of a movable treatment delivery device 140 in order to compensate for movement of a treatment target in a patient supported by stationary patient support.

Figure 2C:
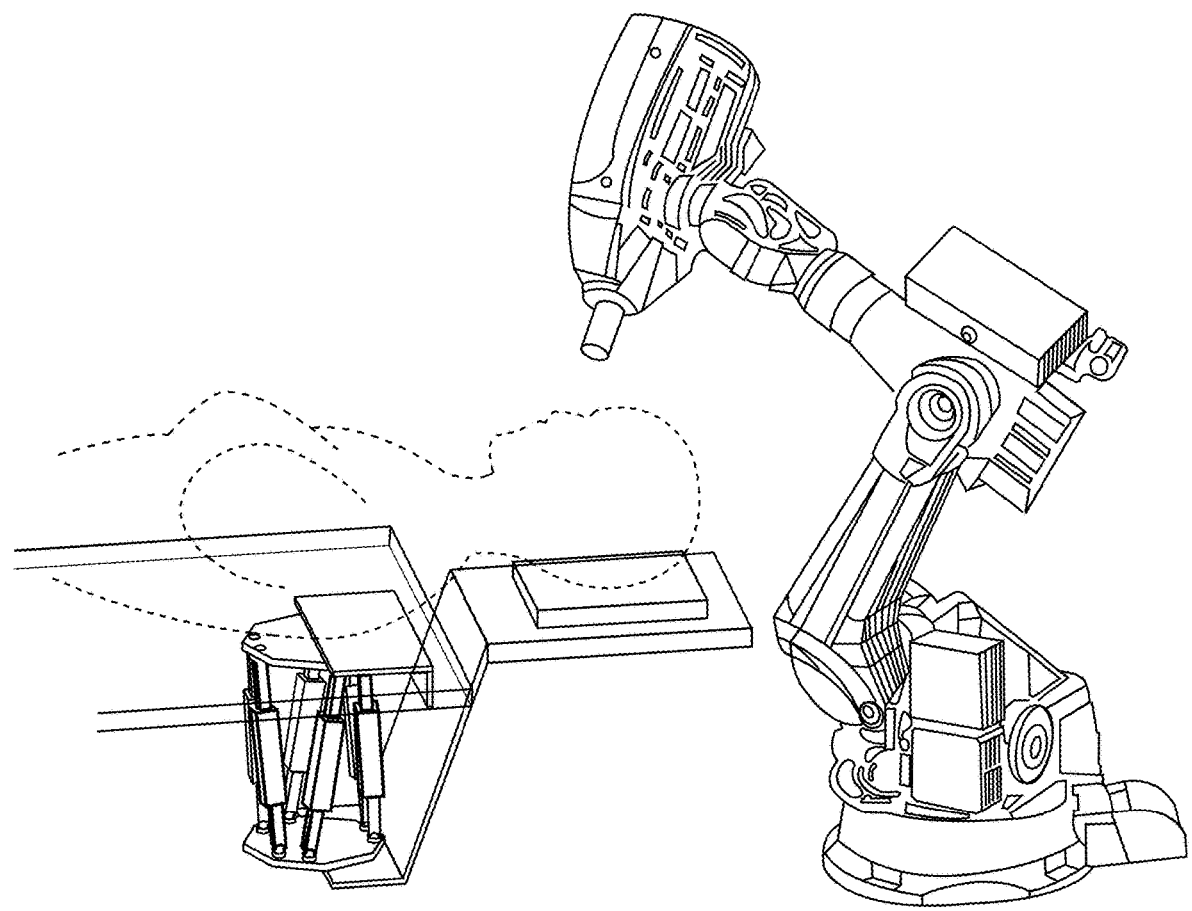
FIG. 2C illustrates a system set-up including a kinematics robot configured to move both a patient and a treatment device.

In particular embodiments, both a platform 120 and a treatment device 140 are end-effectors of kinematics robots, as shown in FIG. 2C. Both the platform 120 and treatment device 140 may be move in a coordinated fashion to maintain the clinical target and treatment in alignment using the methods described in this disclosure. In particular embodiment, a single setup as shown in FIG. 2C may be appropriately configured to (1) motion compensate both the platform 120 and treatment device 140 simultaneously, (2) motion compensate platform 120 while maintaining treatment device 140 stationary, or (3) motion compensate treatment device 140 while maintaining platform 120 stationary.

Treatment delivery device 140 may be any suitable device or machine for applying patient treatment. By way of example, therapy machine 140 may be a linear accelerator (LINAC) machine, a Gamma Knife® machine, Cyber Knife® machine, a proton beam machine, a Magnetic Resonance Imaging (MRI) machine, Computed Tomography (CT) machine, a Positron Emission Tomography (PET) machine, etc. Clinical target 122 may be any body part, tissue, tumor, mass, etc. receiving treatment from a treatment delivery device 140, e.g., a tumor on a patient's brain, lung, breast, etc. As an example, a set-up similar to the one shown in FIG. 2B may be used to move a patient's chest or entire body during a lung radiation treatment for lung tumors. In another example, a set-up similar to the one shown in FIGS. 2A and 4 may be used to move a patient's head during a brain radiation treatment for brain tumors.

Computing device 150 may communicate with other devices, such as kinematics robot 110 and movement sensor 130 through any suitable communications media, such as wired or wireless connections (e.g., USB, serial connections, parallel connections, Bluetooth, WiFi, etc.) or network connections (e.g., LAN, WAN, Internet, etc.). In particular embodiments, computing device 150 may be a remote computing device communicating with system 100 devices through a remote connection (e.g., a cloud computing system).

Figure 4:
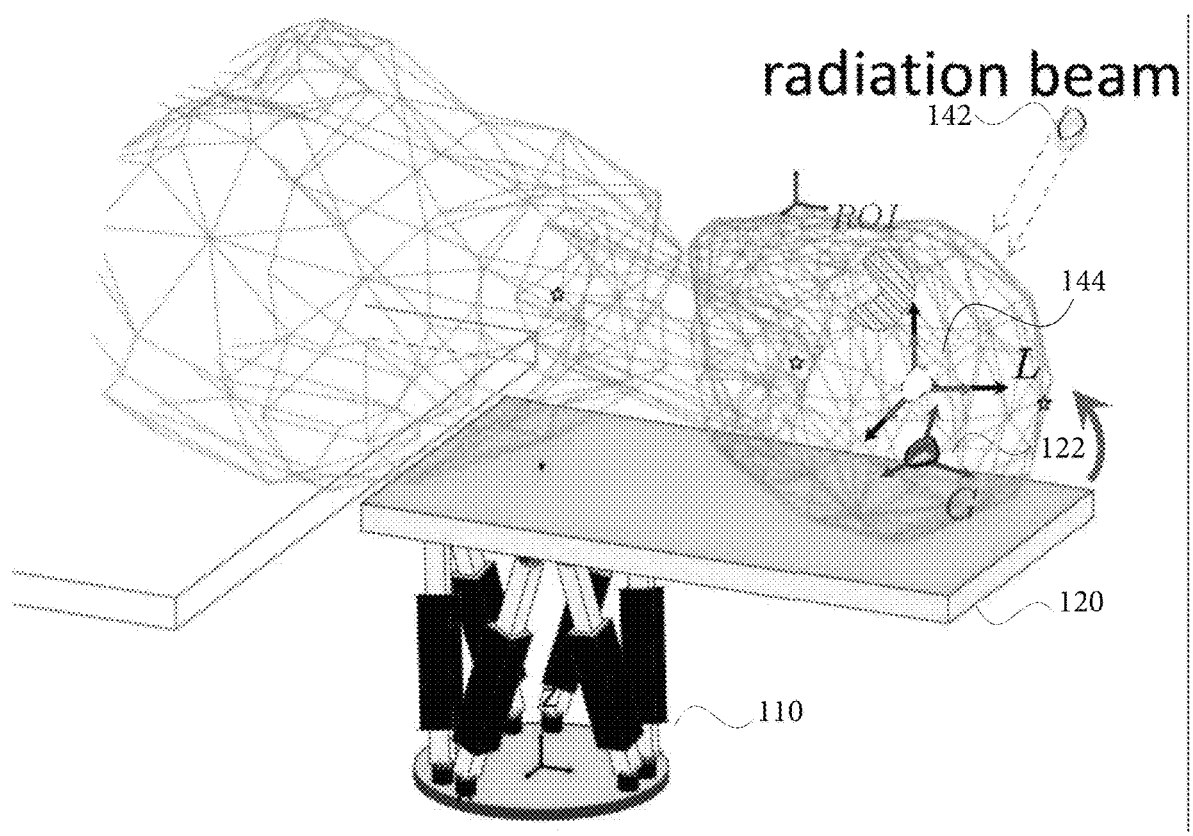
FIG. 4 illustrates a coordinate system for motion stabilization during treatment procedures, according to example embodiments.

FIG. 4 illustrates a coordinate system for motion stabilization during treatment procedures, according to example embodiments. As an example, a patient that is receiving radiation from a radiation beam at a clinical target (e.g., a tumor in his/her brain) may suddenly move out of position. For example, the patient may perform a suddenly unexpected movement (e.g., fidgeting, sneezing, etc.) or a periodic predictable movement (e.g., breathing). When the patient moves, the radiation beam may no longer be treating the tumor and may instead be targeting healthy regions of the brain. Thus, a motion stabilization method may be used to detect the patient's motion and responsively control kinematics robot 112 to move support surface 120 so as to reposition the clinical target to the desired position.

The initial target (G) position 122 (e.g., current position of the brain tumor) can be specified by 6DoF coordinates that include the linear position r=(x, y, z) and the orientation ψ=(pitch, roll, yaw). For a given measured initial target position with a displacement away from the desired set point (L) 144 (e.g., position where the target would receive the desired radiation from the radiation beam), computing device 150 may compute what is the desirable robot end-effector position for returning the target back to the set point.

Figure 5:
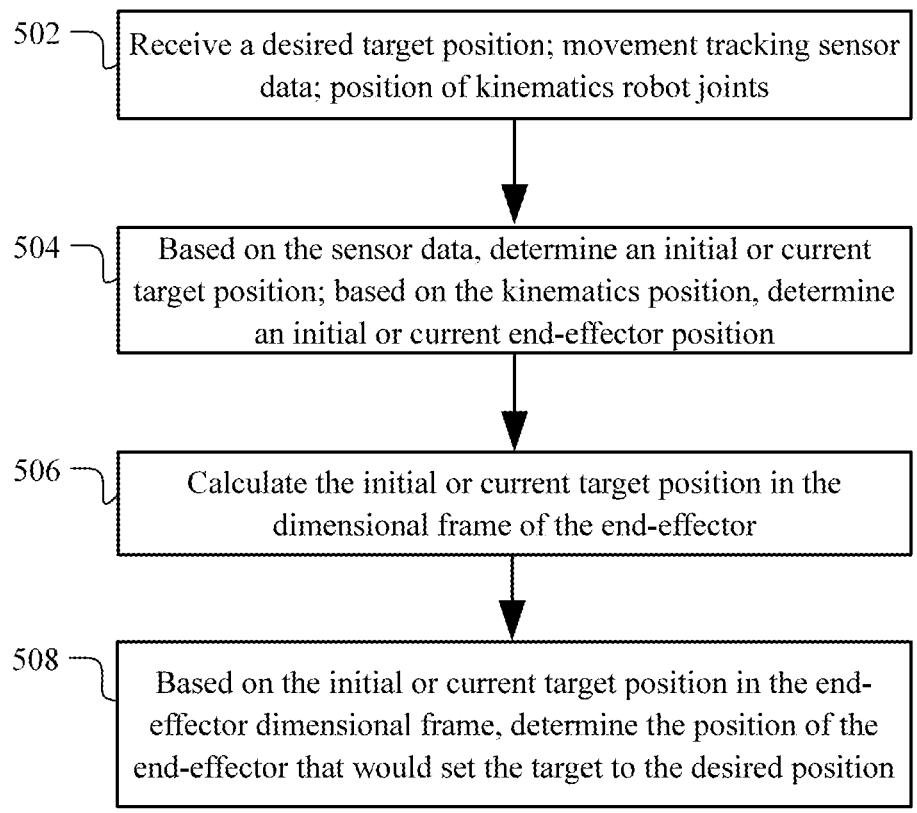
FIG. 5 shows a flowchart describing a method for determining the desirable end-effector position that returns the target back to the desired set point, according to an example embodiment.

FIG. 5 shows a flowchart describing a method 500 for determining the desirable end-effector position that returns the target back to the desired set point, according to an example embodiment. At step 502, computing device 150 receives a desired target position 144, data from movement tracking sensor 130, and the position of the joints of kinematics robot 110 (e.g., the current length of the actuator legs 112 of the robot). As an example, computing device 150 may determine a desired target position 144 based on a direction of a treatment applicator beam. The position of kinematics robot 130 may be received from data obtained from robot 110, may be configured into computing device 150, or may be known from a prior adjustment of the position by computing device 150. At step 504, computing device 150 determines an initial or current target position and an initial or current end-effector position. As an example, computing device 150 may determine the current target position from data obtained from measurements of movement tracking sensor 130, using any suitable image processing techniques. Computing device 150 may determine an end-effector position from a position of the joints of kinematics robot 110. As an example, computing device 150 may convert the lengths of each of the robot's actuator legs 112 into 6DoF dimensions in the end-effector dimensional space.

At step 506, computing device 150 calculates the initial or current target position in the dimensional frame of the end-effector. Suppose the measured initial target position 122 is ($r_g$, $\psi_g$), and the position of the end-effector 120 of the robot at this moment is ($r_u$, $\psi_u$). The initial target position in the end-effector frame ($r_{gu}$, $\psi_{gu}$) may be updated periodically at fixed intervals. Then, $$r_g = r_u + \Omega(\psi_u)^T r_{gu} \qquad (1)$$

$$\Omega(\psi_g) = \Omega(\psi_{gu})\Omega(\psi_u)$$

where $\Omega(\cdot)$ is the direction cosine matrix, and ($r_{gu}$, $\psi_{gu}$) is the initial target position in the end-effector frame, as shown in FIG. 5. The position ($r_{gu}$, $\psi_{gu}$) can be calculated by using the current end-effector position and the measured target position.

At step 508, computing device 150 may determine the position of the end-effector that would set the target 122 to the desired position 144. Assume that the target position with respect to the end-effector remains unchanged during each robot time cycle, it can be verified that by moving the end-effector to the following position ($\hat{r}_u$, $\hat{\psi}$), $$\hat{r}_u = \hat{r}_g - \Omega(\hat{\psi}_u)^T r_{gu} \quad (2)$$

$$\Omega(\hat{\psi}_u) = \Omega(\psi_{gu})^T \Omega(\hat{\psi}_g)$$

the target 122 will move to the desired position 144.

For easy reference, let us denote the 6DoF target and end-effector position vectors as $x:=(r_g; \psi_g)$ and $u:=(r_u; \psi_u)$, respectively. Here (y;z) is used to denote the column vector $(y^T z^T)^T$. Denote initial positions as $x_o = x(0)$ and $u_o = u(0)$. Denote the desired target position as $\hat{x}:=(\hat{r}_g; \hat{\psi}_g)$, the position of end-effector that push the target back to the desired position as $\hat{u}:=(\hat{r}_u; \hat{\psi}_u)$.

Once the start and end positions of the end-effector are known, the system may design a suitable trajectory between these two points. For reference, a path denotes the locus of points in a space and is a geometric description of motion, while a trajectory is a path with timing information. The trajectory in target space may be calculated to converge to the desired position in an optimal way, for example, such that minimum time, shortest path, or steepest descent of the position error is maintained. In this manner, the system can avoid unnecessary overtreating a clinical target. For example, the system can avoid exposure of healthy brain tissue to high doses of radiation and poor tumor conformity.

To solve this problem, trajectory planning may be considered in three different spaces: joint space, operational space, or target space. Joint space may be defined as the robot's joint positions (leg 132 lengths), and allows kinematic constraints to be specified on actuators. As an example, a point in joint space for a six-legged robot may be determined with six numbers, each representing the length of one of the legs. Actuator mechanical constraints may specify the limits and capabilities of the actuators, for example, the maximum length of the legs, the minimum motion in one step etc. Operational space may be defined as the end-effector position in 6DoF (e.g., support surface 120), and allows dynamic constraints to be specified on velocities and accelerations. System dynamic constraints may specify the limits and capabilities of the system's dynamics, for example, the maximum velocity and acceleration in particular trajectories. Actuator mechanical constraints and system dynamic constraints may result in trajectories that are non-intuitive and seemingly non-optimal from a purely spatial perspective. As an example, although a straight line may be the shortest path (distance-wise) between the source and destination of the target, a robot's design may cause a straight line movement to be slow. For example, moving the actuator's legs to create a straight line motion may require a lot of precise movements. Therefore, taking the system's dynamic constraints into account, a non-straight path may reduce the amount of healthy tissue that is exposed to radiation, and the time that the healthy tissue is exposed to radiation.

Finally, target space is defined as the 6DoF position of the target. For example, when the end-effector moves along a trajectory in the operational space, $u(k)$, $k=0, 1, \ldots, n$ with $u(0)=u_o$ and $u(n)=\hat{u}$ for certain n, the target will approach the desired position following a certain trajectory in the target space, $x(k)$, $k=0, 1, \ldots, n$ with $x(0)=x_o$ and $x(n)=\hat{x}$. To implement such an end-effector trajectory, the leg length should thus follow a certain trajectory in the joint space, $L(k)$, $k=0, 1, \ldots, n$ with $L(0)=L_o$ and $L(n)=\hat{L}$.

In particular embodiments, the trajectory may be designed to satisfy control objectives that are subject to the robot's mechanical constraints. For example, the dynamic constraints can be specified in operational space where the maximum 6DoF motion of the end-effector in one step is a vector $v_{max}$, such that, $$-v_{max} \leq u(k) - u(k-1) \leq v_{max}. \quad (3)$$

In particular embodiments, a trajectory may be designed that optimizes both spatial and temporal performance. The trajectory may be computed in real-time or quasi-real-time by use of any suitable optimization algorithm, such as, by way of example, the quasi-Newtonian Limited-Broyden-Fletcher-Goldfarb-Shannon (L-BFGS) algorithm as described in J. L. Morales and J. Nocedal, "Remark on algorithm 778: L-BFGS-B: Fortran subroutines for large-scale bound constrained optimization," *ACM Transactions on Mathematical Software (TOMS)*, vol. 38, no. 1, p. 7, 2011, which is incorporated herein by reference in its entirety. In particular embodiments, the trajectory may also be computed using interpolation techniques.

Figure 6:
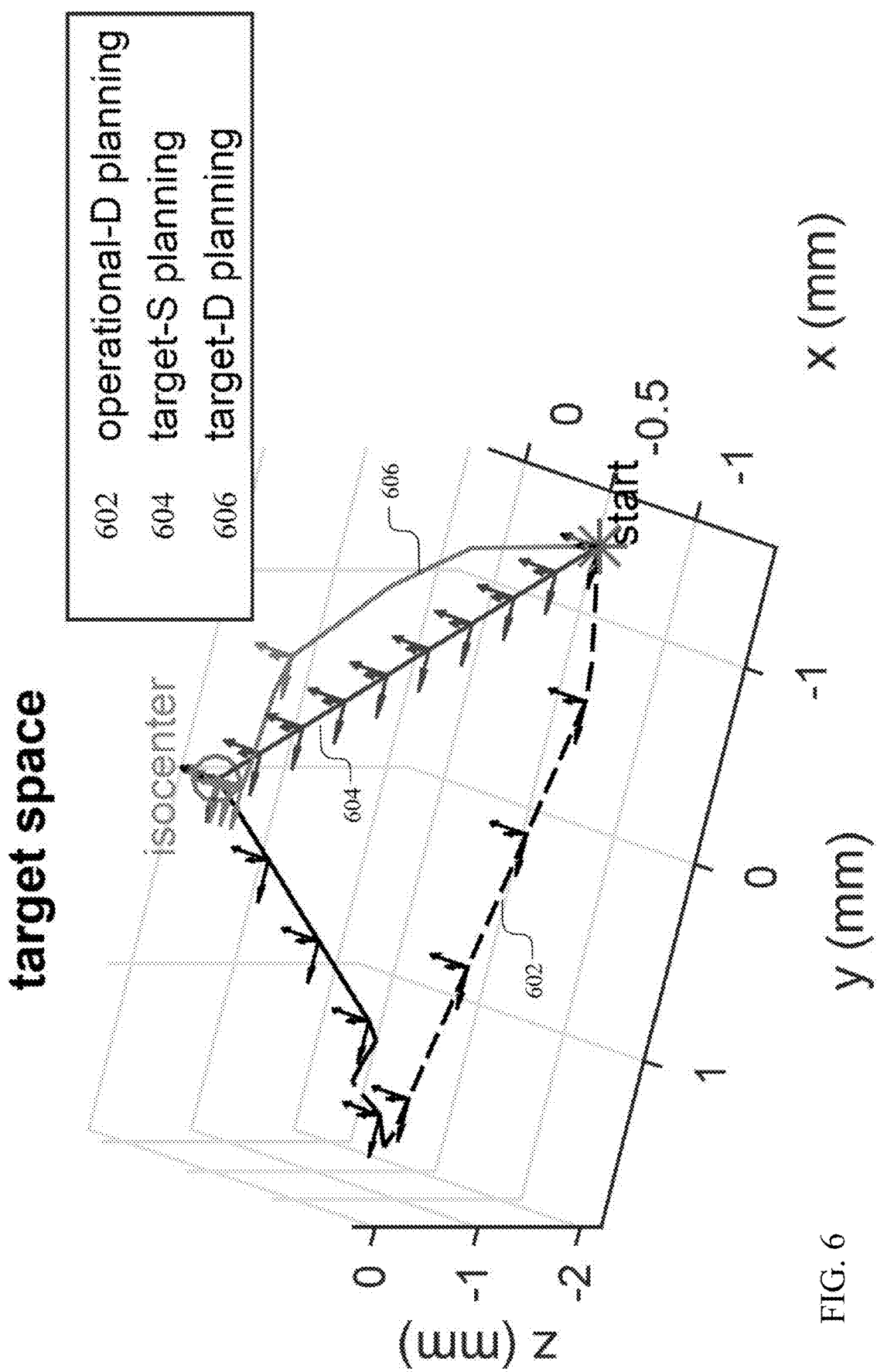
FIG. 6 shows planned trajectories for moving a clinical target to a desired set point, according to an example embodiment.

Given the initial and desired end-effector position, $u_o$ and $\hat{u}$, the trajectory planning can be considered directly in the operational space. One way to move the end-effector from the initial position to the desired position may be through a straight path in the operational space. The end-effector position $u(k)$ may be linearly interpolated between $u_o$ and $\hat{u}$. Denote it as operational-S planning. One way may be to use a control algorithm to push each coordinate of end-effector to the desired value $\hat{u}$ as fast as possible in each step, i.e., to achieve the steepest descent on end-effector position error. Refer such a planning as operational-D planning, as shown in curve 602 of FIG. 6. However, operational-D planning could lead to a target trajectory that has an even larger target error than the initial error, and the resulted target trajectory could have a large overall trajectory error.

In particular embodiments, to facilitate trajectory planning in the target space, the movement compensation system may be first discretized and linearized. Assume that the target position keeps unchanged with respect to the end-effector, i.e., $(r_{gu}, \psi_{gu})$ is constant, then (1) can be represent as $x=f(u)$, where x and u are the 6DoF position vectors of the target and the end-effector, respectively. The discrete system is given by $$x(k)=f(u(k)). \quad (4)$$

The problem can be approximated as a problem on linear system, i.e., a system of linear equations. The linearization may be performed in each time cycle, so it can describe the system in each small motion accurately. The time cycle can be any suitable time cycle for a desired accuracy of movement compensation. In particular embodiments, the time cycle is the time for the smallest movement step that kinematics robot 110 can perform. In a general sense, the trajectory planning in the target space can be formulated as:

minimize $\Sigma_{k=0}^{\infty} h(x(k), \hat{x}, u(k))$

Consider $x(k+1)=f(u(k+1))$ and small end-effector motion in each step $v(k)=u(k+1)-u(k)$. By linearization, the motion compensation discrete system is given by $$x(k+1)=x(k)+Av(k), \quad (5)$$

where the matrix A $$A = \frac{\partial f}{\partial u}\bigg|_{r_u, \varphi_u, r_{gu}, \varphi_{gu}(k)}$$

depends on both $(r_u, \psi_u)$ and $(r_{gu}, \psi_{gu})$ of moment k, and can be updated in each step. The target can move back to the desired position following a straight line in the target space. Refer to such planning as target-S planning, shown in curve 604 of FIG. 6. Note that the motion for operational-S planning and target-S planning are about the same for the compensation of a small target displacement.

Although moving through the shortest path, target-S planning may not exploit the robot's potential in reducing the target's displacement. In particular embodiments, the trajectory with the steepest descent of target position error in each step can be achieved by formulating the problem as an optimization problem with the following objective function, $$\text{minimize } (x+Av-\hat{x})^T(x_o+Av-\hat{x}),$$

$$\text{subject to } -v_{max} \leq v \leq v_{max}. \quad (7)$$

For each step, $x_o$ is updated, $x_o=x(k-1)$, and according to (5), the next step target position is $x(k)=x_o+Av$, where the vector v is the end-effector motion to be optimized. Refer such a planning as target-D planning, as shown in curve 606 of FIG. 6.

One reason to consider optimization in each step as in (7) rather than over the whole trajectory is due to the weak coupling between target and end-effector. In particular embodiments, the target position with respect to end-effector frame could change in each step. Re-computing the trajectory step-by-step may allow for faster reaction to movement, thus providing better motion compensation in real-time or quasi-real-time.

While trajectory planning using operational-D planning, target-S planning and target-D planning have been described herein, this disclosure contemplates any suitable optimization based trajectory planning with a modified objective function. In particular embodiments, the objective function may be modified to embed additional control objectives and robot mechanical constraints. As an example, additional constraints may be specified to achieve moving the target to the desired destination is the shortest time. To achieve minimum-time control, the constraint may be imposed as, $$-(\kappa-1)v_{max} \leq \hat{u}-u_o-v \leq (\kappa-1)v_{max}$$

where $\kappa=\max|(\hat{u}-u_o)/v_{max}|$.

In another example, additional constraints may be specified for imposing an end-effector acceleration limit. In another example, the objective function may be specified to achieve a tradeoff between a straight trajectory and a target error steepest descent trajectory by using a weighted scale function. An example of a modified objective function to achieve this tradeoff may be, $$\text{minimize } (x_o + Av - \hat{x})^T(x_o + Av - \hat{x}) +$$

$$\rho(Av - (\hat{x}-x_o)/\kappa)\rho\left(Av - \frac{\hat{x}-x_o}{\kappa}\right)^T\left(Av - \frac{\hat{x}-x_o}{\kappa}\right)$$

$$\text{subject to } -v_{max} \leq v \leq v_{max}.$$

In particular embodiments, the treatment delivery device 140 is set in motion by a robot 110, and a patient platform is kept stationary, as previously explained. The same methods and systems described above and below can be used to perform 6DoF correction trajectory of a movable treatment delivery device 140 in order to compensate for movement of a treatment target in a patient supported by stationary patient support. In this scenario, operational space may be defined as the treatment delivery device position in 6DoF, again allowing dynamic constraints to be specified on velocities and accelerations. Joint space may refer to actuators of a robot 110 controlling movement of the treatment delivery device 140. Target space may refer to the 6DoF position of the clinical target. Using the techniques above, interpolation or optimization may thus be used to compute a trajectory that moves the treatment delivery device 140 from a starting position to a target position by minimizing the positional error at each step.

Figure 7:
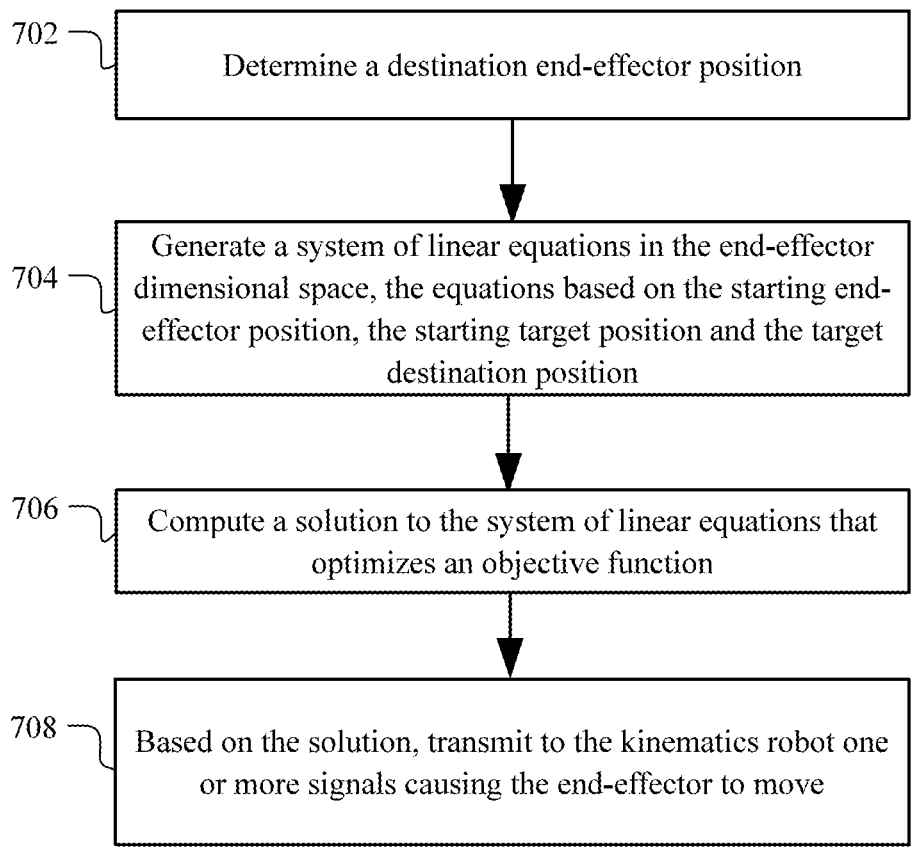
FIG. 7 is a flowchart for a method for performing real-time motion stabilization for treatment procedures, according to an example embodiment

FIG. 7 is a flowchart for a method 700 for performing a 6 degree-of-freedom (6DoF) correction trajectory in order to compensate movement of a treatment target in a patient supported by a patient support end-effector. Method 700 can be performed by processing logic that can comprise hardware (e.g., kinematics robot, motion tracking sensor, circuitry, dedicated logic, programmable logic, microcode, etc.), software (e.g., instructions run on a processing device), or any combination thereof. At step 702, computing device 150 receives a starting end-effector position in six degrees-of-freedom (6DoF) associated with an end-effector, a starting target position in 6DoF associated with a clinical target, and a target destination position in 6DoF associated with a desired target position, the target destination position corresponding to a position in space receiving targeted treatment from a treatment delivery device. At step 704, computing device 150 determines a destination end-effector position in 6DoF associated with the end-effector, wherein positioning the end-effector on the destination end-effector position causes the target to be positioned on the target destination position. At step 706, computing device 150, calculates a trajectory between the starting end-effector position associated with the end-effector and the destination end-effector position associated with the end-effector, the trajectory being calculated based on an objective function. At step 708, computing device 150 transmits, to a mechanical device controlling movement of the end-effector, one or more signals causing the end-effector to move from the starting end-effector position to the destination end-effector position along the determined trajectory.

Figure 8:
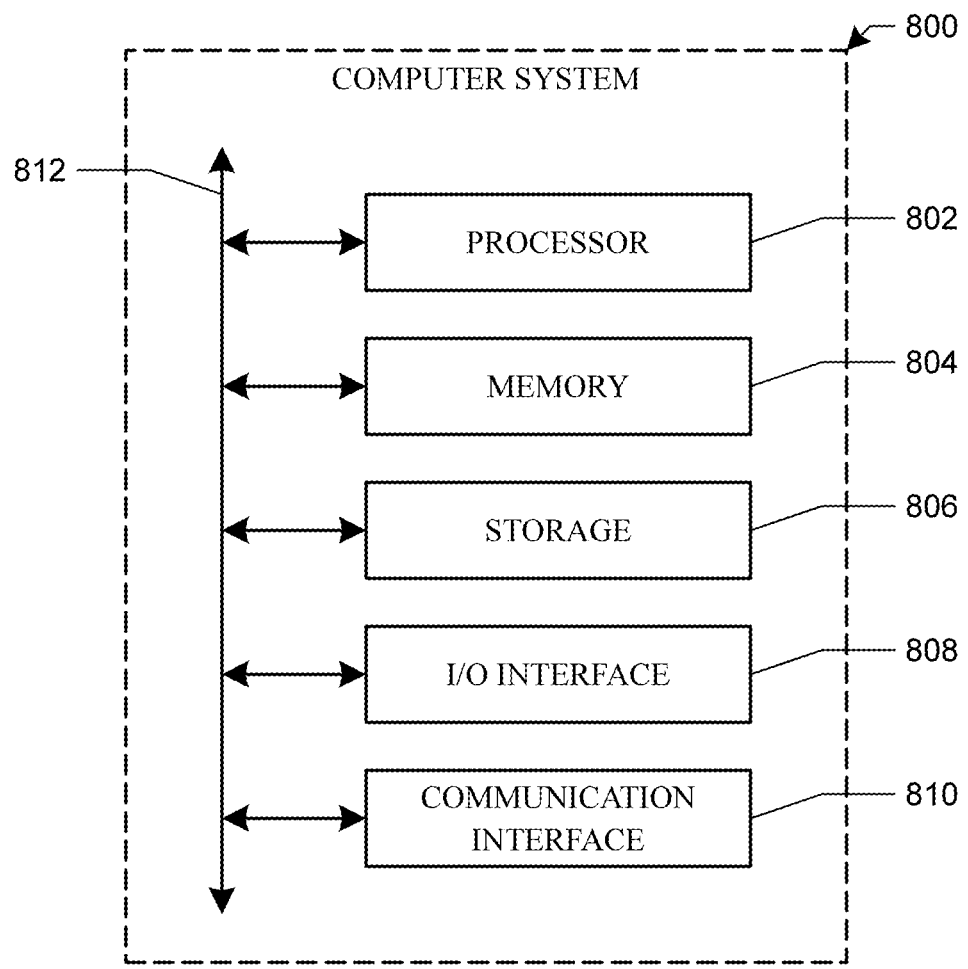
FIG. 8 is an example computer system useful for implementing various embodiments.

FIG. 8 illustrates an example computer system 800. In particular embodiments, one or more computer systems 800 perform one or more steps of one or more methods described or illustrated herein. In particular embodiments, one or more computer systems 800 provide functionality described or illustrated herein. In particular embodiments, software running on one or more computer systems 800 performs one or more steps of one or more methods described or illustrated herein or provides functionality described or illustrated herein. Particular embodiments include one or more portions of one or more computer systems 800. Herein, reference to a computer system may encompass a computing device, and vice versa, where appropriate. Moreover, reference to a computer system may encompass one or more computer systems, where appropriate.

This disclosure contemplates any suitable number of computer systems 800. This disclosure contemplates computer system 800 taking any suitable physical form. As example, computer system 800 may be an embedded computer system, a desktop computer system, a laptop or notebook computer system, a mainframe, a mobile telephone, a personal digital assistant (PDA), a server, a tablet computer system, or a combination of two or more of these. Where appropriate, computer system 800 may include one or more computer systems 800; be unitary or distributed; span multiple locations; span multiple machines; span multiple data centers; or reside in a cloud, which may include one or more cloud components in one or more networks. Where appropriate, one or more computer systems 800 may perform without substantial spatial or temporal limitation one or more steps of one or more methods described or illustrated herein. As an example, one or more computer systems 800 may perform in real time or in batch mode one or more steps of one or more methods described or illustrated herein. One or more computer systems 800 may perform at different times or at different locations one or more steps of one or more methods described or illustrated herein, where appropriate.

In particular embodiments, computer system 800 includes a processor 802, memory 804, storage 806, an input/output (I/O) interface 808, a communication interface 810, and a bus 812. Although this disclosure describes and illustrates a particular computer system having a particular number of particular components in a particular arrangement, this disclosure contemplates any suitable computer system having any suitable number of any suitable components in any suitable arrangement.

In particular embodiments, processor 802 includes hardware for executing instructions, such as those making up a computer program. As an example, to execute instructions, processor 802 may retrieve (or fetch) the instructions from an internal register, an internal cache, memory 804, or storage 806; decode and execute them; and then write one or more results to an internal register, an internal cache, memory 804, or storage 806. In particular embodiments, processor 802 may include one or more internal caches for data, instructions, or addresses. This disclosure contemplates processor 802 including any suitable number of any suitable internal caches, where appropriate. In particular embodiments, processor 802 may include one or more internal registers for data, instructions, or addresses. This disclosure contemplates processor 802 including any suitable number of any suitable internal registers, where appropriate. Where appropriate, processor 802 may include one or more arithmetic logic units (ALUs); be a multi-core processor; or include one or more processors 802. Although this disclosure describes and illustrates a particular processor, this disclosure contemplates any suitable processor.

In particular embodiments, memory 804 includes main memory for storing instructions for processor 802 to execute or data for processor 802 to operate on. As an example, computer system 800 may load instructions from storage 806 or another source (such as, for example, another computer system 800) to memory 804. Processor 802 may then load the instructions from memory 804 to an internal register or internal cache. To execute the instructions, processor 802 may retrieve the instructions from the internal register or internal cache and decode them. During or after execution of the instructions, processor 802 may write one or more results (which may be intermediate or final results) to the internal register or internal cache. Processor 802 may then write one or more of those results to memory 804. In particular embodiments, processor 802 executes only instructions in one or more internal registers or internal caches or in memory 804 (as opposed to storage 806 or elsewhere) and operates only on data in one or more internal registers or internal caches or in memory 804 (as opposed to storage 806 or elsewhere). One or more memory buses (which may each include an address bus and a data bus) may couple processor 802 to memory 804. Bus 812 may include one or more memory buses, as described below. In particular embodiments, memory 804 includes random access memory (RAM). This RAM may be volatile memory, where appropriate Memory 804 may include one or more memories 804, where appropriate. Although this disclosure describes and illustrates particular memory, this disclosure contemplates any suitable memory.

In particular embodiments, storage 806 includes mass storage for data or instructions. As an example, storage 806 may include a hard disk drive (HDD), a floppy disk drive, flash memory, an optical disc, a magneto-optical disc, magnetic tape, or a Universal Serial Bus (USB) drive or a combination of two or more of these. Storage 806 may include removable or non-removable (or fixed) media, where appropriate. Storage 806 may be internal or external to computer system 800, where appropriate. In particular embodiments, storage 806 is non-volatile, solid-state memory. In particular embodiments, storage 806 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 806 taking any suitable physical form. Storage 806 may include one or more storage control units facilitating communication between processor 802 and storage 806, where appropriate. Where appropriate, storage 806 may include one or more storages 806. Although this disclosure describes and illustrates particular storage, this disclosure contemplates any suitable storage.

In particular embodiments, I/O interface 808 includes hardware, software, or both, providing one or more interfaces for communication between computer system 800 and one or more I/O devices. Computer system 800 may include one or more of these I/O devices, where appropriate. One or more of these I/O devices may enable communication between a person and computer system 800. As an example, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 808 for them. Where appropriate, I/O interface 808 may include one or more device or software drivers enabling processor 802 to drive one or more of these I/O devices. I/O interface 808 may include one or more I/O interfaces 808, where appropriate. Although this disclosure describes and illustrates a particular I/O interface, this disclosure contemplates any suitable I/O interface.

In particular embodiments, communication interface 810 includes hardware, software, or both providing one or more interfaces for communication (such as, for example, packet-based communication) between computer system 800 and one or more other computer systems 800 or one or more networks. As an example, communication interface 810 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 810 for it. As an example, computer system 800 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 800 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 800 may include any suitable communication interface 810 for any of these networks, where appropriate. Communication interface 810 may include one or more communication interfaces 810, where appropriate. Although this disclosure describes and illustrates a particular communication interface, this disclosure contemplates any suitable communication interface.

In particular embodiments, bus 812 includes hardware, software, or both coupling components of computer system 800 to each other. As an example, bus 812 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 812 may include one or more buses 812, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. A computer-implemented method comprising, by at least one processor:

receiving a starting end-effector position in six degrees-of-freedom (6DoF) associated with an end-effector at each one of a plurality of cycles, a starting target position in 6DoF associated with a clinical target, and a target destination position in 6DoF associated with a desired target position, the target destination position corresponding to a position in space receiving targeted treatment from a treatment delivery device, wherein movement of the end-effector effects movement of the clinical target;

determining a destination end-effector position in 6DoF associated with the end-effector, wherein positioning the end-effector on the destination end-effector position would cause the target to be positioned on the target destination position;

calculating, at each one of the plurality of cycles in a real-time manner and using a quasi-Newtonian Limited-Broyden-Fletcher-Goldfarb-Shannon (L-BFGS) algorithm, a 6DoF trajectory between the starting end-effector position associated with the end-effector and the destination end-effector position associated with the end-effector, wherein the trajectory comprises a plurality of discrete or continuous steps and wherein the calculating the 6DoF trajectory comprises solving an optimization problem to minimize a correction distance and a time to the target destination position that is subjected to actuator mechanical constraints and system dynamical constraints, the optimization problem determining a next end-effector position associated with a next step in the trajectory;

transmitting, to a mechanical device controlling movement of the end-effector, one or more signals causing the end-effector to move from the starting end-effector position to the destination end-effector position along the determined trajectory, wherein the mechanical device comprises a kinematics robot system having a plurality of actuators, and wherein the one or more signals cause actuators to change the length of one or more of the plurality of actuators; and utilizing a motion stabilization method to:
  detect a motion of the clinical target away from the destination end-effector position; and
  transmit, to the kinematics robot system, one or more additional signals to modify, in real-time, a length of the one or more of the plurality of actuators to reposition the clinical target to the desired end-effector position.

2. The method of claim 1, wherein the trajectory comprises a plurality of discrete steps and wherein the calculating the 6DoF trajectory comprises determining the discrete steps by interpolating between the starting target position and the target destination position.

3. The method of claim 1, wherein the transmitting comprises:
  transmitting, to a mechanical device controlling movement of the end-effector, one or more signals causing the end-effector to move from the starting end-effector position to the next end-effector position,
  wherein the method further comprises repeating the determining the next end-effector position and transmitting signals causing the end-effector to move to the next end-effector position so as to cause the end-effector to move from the starting end-effector position to the destination end-effector position along the determined trajectory in a step-by-step manner.

4. The method of claim 1, wherein the calculating the 6DoF trajectory comprises minimizing a time integral of a target position error along the target trajectory, wherein the target position error comprises a difference between the starting target position and the destination target position.

5. The method of claim 1, wherein the trajectory comprises a shortest-path trajectory between the starting end-effector position and the destination end-effector position.

6. The method of claim 1, wherein the trajectory comprises a target error steepest-descent trajectory between the starting end-effector position and the destination end-effector position.

7. The method of claim 1, wherein the trajectory comprises a weighted combination of a short-path trajectory and a steepest-descent trajectory between the starting end-effector position and the destination end-effector position.

8. A system, comprising:
  a mechanical device coupled to an end-effector; and
  a memory and at least one processor coupled to the memory, the processor configured to:
    receive a starting end-effector position in six degrees-of-freedom (6DoF) associated with an end-effector at each one of a plurality of cycles, a starting target position in 6DoF associated with a clinical target, and a target destination position in 6DoF associated with a desired target position, the target destination position corresponding to a position in space receiving targeted treatment from a treatment delivery device, wherein movement of the end-effector effects movement of the clinical target;
    determine a destination end-effector position in 6DoF associated with the end-effector, wherein positioning the end-effector on the destination end-effector position would cause the target to be positioned on the target destination position;
    calculate, at each one of the plurality of cycles in a real-time manner and using a quasi-Newtonian Limited-Broyden-Fletcher-Goldfarb-Shannon (L-BFGS) algorithm, a 6DoF trajectory between the starting end-effector position associated with the end-effector and the destination end-effector position associated with the end-effector, wherein the trajectory comprises a plurality of discrete or continuous steps and wherein the calculating the 6DoF trajectory comprises solving an optimization problem to minimize a correction distance and a time to the target destination position that is subjected to actuator mechanical constraints and system dynamical constraints, the optimization problem determining a next end-effector position associated with a next step in the trajectory;
    transmit, to a mechanical device controlling movement of the end-effector, one or more signals causing the end-effector to move from the starting end-effector position to the destination end-effector position along the determined trajectory,
    wherein the mechanical device comprises a kinematics robot system having a plurality of actuators, and
    wherein the one or more signals cause actuators to change the length of one or more of the plurality of actuators; and
    utilize a motion stabilization method to:
      detect a motion of the clinical target away from the destination end-effector position; and
      transmit, to the kinematics robot system, one or more additional signals to modify, in real-time, a length of the one or more of the plurality of actuators to reposition the clinical target to the desired end-effector position.

9. The system of claim 8, wherein the trajectory comprises a plurality of discrete steps and wherein the calculating the 6DoF trajectory comprises determining the discrete steps by interpolating between the starting target position and the target destination position.

10. The system of claim 8, wherein, the interpolation or optimization methods are based on the starting end-effector position, the starting target position, and the target destination position, and the interpolation or optimization methods optimize an end-effector motion.

11. The system of claim 8, wherein to transmit the one or more signals the processor is further configured to:
  transmit, to a mechanical device controlling movement of the end-effector, one or more signals causing the end-effector to move from the starting end-effector position to the next end-effector position,
  wherein the processor is further configured to repeatedly determine the next end-effector position and transmit signals causing the end-effector to move to the next end-effector position so as to cause the end-effector to move from the starting end-effector position to the destination end-effector position along the determined trajectory in a step-by-step manner.

12. A non-transitory computer-readable device having instructions stored thereon that, when executed by at least one computing device, causes the at least one computing device to perform operations comprising:
  receiving a starting end-effector position in six degrees-of-freedom (6DoF) associated with an end-effector at each one of a plurality of cycles, a starting target position in 6DoF associated with a clinical target, and a target destination position in 6DoF associated with a desired target position, the target destination position corresponding to a position in space receiving targeted treatment from a treatment delivery device, wherein movement of the end-effector effects movement of the clinical target;

determining a destination end-effector position in 6DoF associated with the end-effector, wherein positioning the end-effector on the destination end-effector position would cause the target to be positioned on the target destination position;

calculating, at each one of the plurality of cycles in a real-time manner and using a quasi-Newtonian Limited-Broyden-Fletcher-Goldfarb-Shannon (L-BFGS) algorithm, a 6DoF trajectory between the starting end-effector position associated with the end-effector and the destination end-effector position associated with the end-effector, wherein the trajectory comprises a plurality of discrete or continuous steps and wherein the calculating the 6DoF trajectory comprises solving an optimization problem to minimize a correction distance and a time to the target destination position that is subjected to actuator mechanical constraints and system dynamical constraints, the optimization problem determining a next end-effector position associated with a next step in the trajectory;

transmitting, to a mechanical device controlling movement of the end-effector, one or more signals causing the end-effector to move from the starting end-effector position to the destination end-effector position along the determined trajectory,
wherein the mechanical device comprises a kinematics robot system having a plurality of actuators, and
wherein the one or more signals cause actuators to change the length of one or more of the plurality of actuators; and utilizing a motion stabilization method to:
detect a motion of the clinical target away from the destination end-effector position; and
transmit, to the kinematics robot system, one or more additional signals to modify, in real-time, a length of the one or more of the plurality of actuators to reposition the clinical target to the desired end-effector position.

13. A computer-implemented method comprising, by at least one processor:

receiving a starting device position in six degrees-of-freedom (6DoF) associated with a treatment delivery device at each one of a plurality of cycles and a target position in 6DoF associated with a clinical target, the starting device position corresponding to a position in space receiving targeted treatment from a treatment delivery device;

determining a destination device position in 6DoF associated with the treatment delivery device, wherein positioning the treatment delivery device on the destination device position would cause the treatment to be delivered to the target position;

calculating, at each one of the plurality of cycles in a real-time manner and using a quasi-Newtonian Limited-Broyden-Fletcher-Goldfarb-Shannon (L-BFGS) algorithm, a 6DoF trajectory between the starting device position and the destination device position, wherein the trajectory comprises a plurality of discrete or continuous steps and wherein the calculating the 6DoF trajectory comprises solving an optimization problem to minimize a correction distance and a time to the target destination position that is subjected to actuator mechanical constraints and system dynamical constraints, the optimization problem determining a next end-effector position associated with a next step in the trajectory;

transmitting, to a mechanical device controlling movement of the treatment delivery device, one or more signals causing the treatment delivery device to move from the starting device position to the destination device position along the determined trajectory,
wherein the mechanical device comprises a kinematics robot system having a plurality of actuators, and
wherein the one or more signals cause actuators to change the length of one or more of the plurality of actuators; and utilizing a motion stabilization method to:
detect a motion of the clinical target away from the destination end-effector position; and
transmit, to the kinematics robot system, one or more additional signals to modify, in real-time, a length of the one or more of the plurality of actuators to reposition the clinical target to the desired end-effector position.

* * * * *